United States Patent [19]

Scott

[11] Patent Number: 5,137,714
[45] Date of Patent: Aug. 11, 1992

[54] ANHYDROUS COSMETIC COMPOSITION COMPRISING STABLE LOWER ALKYL ESTERS OF PYROGLUTAMIC ACID

[75] Inventor: Ian R. Scott, Wellingborough, England

[73] Assignee: Unilever Patent Holdings B.V., Rotterdam, Netherlands

[21] Appl. No.: 683,589

[22] Filed: Apr. 11, 1991

Related U.S. Application Data

[63] Continuation of Ser. No. 351,746, May 15, 1989, abandoned.

[30] Foreign Application Priority Data

May 13, 1988 [GB] United Kingdom ............... 8811409

[51] Int. Cl.⁵ .............................................. A61K 7/48
[52] U.S. Cl. .......................................... 424/63; 424/64; 424/70; 514/423; 514/424; 514/785; 514/873; 514/947

[58] Field of Search .................. 424/61, 63, 64, 70, 424/59; 514/423, 424, 785, 788, 946, 947, 969, 970, 873, 844, 847

[56] References Cited

U.S. PATENT DOCUMENTS

| | | | |
|---|---|---|---|
| 3,235,457 | 2/1966 | Laden | 514/423 X |
| 3,836,665 | 9/1974 | Eberhardt | 514/423 |
| 4,774,255 | 9/1988 | Black et al. | 548/518 X |
| 4,789,667 | 12/1988 | Makino et al. | 514/947 X |
| 4,832,946 | 5/1989 | Green | 424/70 |
| 4,863,952 | 9/1989 | Abe et al. | 514/423 |
| 4,986,982 | 1/1991 | Scott | 424/63 |

FOREIGN PATENT DOCUMENTS 176217 4/1986 European Pat. Off. .

Primary Examiner—Thurman K. Page
Assistant Examiner—James Spear
Attorney, Agent, or Firm—Cushman, Darby & Cushman

[57] ABSTRACT

A non-aqueous drug-free composition for topical application to human skin comprises:
(i) a special ester of pyroglutamic acid; and
(ii) a cosmetically acceptable non-aqueous vehicle.

5 Claims, No Drawings

ANHYDROUS COSMETIC COMPOSITION COMPRISING STABLE LOWER ALKYL ESTERS OF PYROGLUTAMIC ACID

This is a continuation of application Ser. No. 351,746, filed on May 15, 1989, which was abandoned upon the filing hereof.

FIELD OF INVENTION

The invention relates to non-aqueous compositions containing an ester of pyroglutamic acid for topical application to human skin or hair.

BACKGROUND AND PRIOR ART

Pyroglutamic acid (also known as 2-pyrrolidone-5-carboxylic acid) is the principle ingredient of the "natural moisturising factor" that enables the stratum corneum of the skin to maintain a high water content despite low external humidity. Pyroglutamic acid applied topically to the skin has a temporary moisturising effect, but it is easily washed away and gives no long term skin benefit.

The use of certain esters of pyroglutamic acid as auxiliary agents for accelerating absorption of drugs through the skin is described in JA 60-214744 (Nitto Denki Kogyo KK.

Cosmetics containing one or more compounds obtained by the esterification of 2-pyrrolidone-5-carboxylic acid (PCA) and a fatty acid chosen from straight chain higher fatty acids are described in JA 57-185209 (Nisshin Seiyu KK) for contributing to the natural moisturising factor (NMF) present in the horny layer of the skin, part of which NMF is characterised as a salt of PCA.

Certain esters of pyroglutamic acid described in EP-A-0 176 217 (Unilever) are stated to be analogues of naturally occuring N-terminal pyroglutamic peptides. These naturally ocurring peptides are substrates for the enzyme pyroglutamic acid peptidase which represent one route of pyroglutamic acid synthesis in the stratum corneum: [See: J G Barrett and I R Scott (1983), "Pyrrolidone carboxylic acid synthesis in guinea pig epidermis", J Invest. Dermatol. 81, 122].

These esters are stated to penetrate readily into the stratum corneum, and there provide a substrate for this enzyme at the normal site of pyroglutamic acid synthesis, that is, inside the cells of the stratum corneum.

There are, however, certain disadvantages in employing products based on these prior proposals; these are firstly, in aqueous systems, there is a tendency for hydrolysis of the ester of pyroglutamic acid to occur prematurely, so that the free acid, pyroglutamic acid, is present in the composition, and its benefit prior to application to the skin is thereby at best relatively short lived, and secondly, that the presence of drugs in topical products can severely limit their cosmetic usefulness.

We have now discovered that the stability of esters of pyroglutamic acid can be significantly improved and the general cosmetic use widened, by formulating them in a non-aqueous composition (that is one in which the amount of water present does not exceed 5% by weight of the composition), which otherwise contains no molecule that could be classed as a drug, thereby limiting its cosmetic usefulness.

Evidence in support of the preference for a non-aqueous composition to provide enhanced stability for the ester, compared with compositions containing >5% water, is given later in this specification.

We have, furthermore, found that the ester of pyroglutamic acid penetrates more readily into the stratum corneum than does the free acid, the penetrated ester being enzymically cleaved, as already stated, to yield pyroglutamic acid in situ in the stratum corneum, thereby to augment that which occurs naturally in this region of the skin. Evidence to support this observation is give later in this specification.

DEFINITION OF THE INVENTION

Accordingly, the invention provides a non-aqueous drug-free composition for topical application to human skin which comprises:

(i) from 0.01 to 99% by weight of an ester of pyroglutamic acid having the structure:

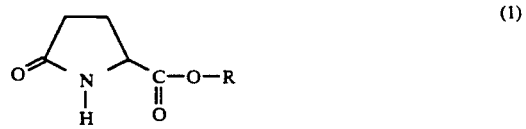

(1)

where R is a linear or branched chain saturated or unsaturated alkyl group having from 1 to 30 carbon atoms, or the group:

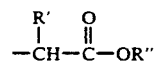

where R' and R" are the same or different and are each represented by H or the group:

(2)

either u or v is 1 and the other of them is zero
w is zero, or an integer of from 1 to 21
x is zero, or an integer of from 1 to 4
y is zero, or an integer of from 1 to 2
z is zero, or an integer of from 1 to 4; and
u+v+w+x+y+z is an integer of from 1 to 22;
the subgroups within the group (2) being in any sequence; provided that when the subgroup (CH=CH) is present, then the total number of carbon atoms in said group (2) will be from 10 to 20; and (ii) from 1 to 99.99% by weight of a cosmetically acceptable non-aqueous vehicle.

DISCLOSURE OF THE INVENTION

It is accordingly an object of the invention to provide a non-aqueous composition which is suitable for topical application to human skin, including the lips, mucosae and scalp, and to human hair, comprising certain esters of pyroglutamic acid in a non-aqueous vehicle.

By "non-aqueous" is meant that the composition according to the invention will contain no more than 5% by weight of water. Preferably, the composition will contain no more that 3%, most preferably no more than 2% by weight of water.

The esters of pyroglutamic acid

Examples of suitable esters of pyroglutamic acid where P in structure (1) is a $C_1$ to $C_{30}$ linear or branched chain alkyl group are:
pyroglutamic acid methyl ester pyroglutamic acid ethyl ester
pyroglutamic acid n-propyl ester
pyroglutamic acid n-butyl ester
pyroglutamic acid n-hexyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradecyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimethyl-1-pentane ester
pyroglutamic acid methyloctyl ester.

Particularly preferred esters of this group are those where R in structure (1) is $C_1$ to $C_{14}$ alkyl, (linear or branched), especially $C_1$ to $C_6$ alkyl (linear or branched).

Examples of the group (2) include straight and branched chain, saturated or unsaturated aliphatic groups having from 1 to 22 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl
arachidyl, and
behenyl;
and the $C_{10-22}$ alkenyl groups:
linoleyl
linolenyl
δ-linolenyl
arachidonyl, and
columbinyl.

Examples of the group (2) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

Further specific examples of esters of pyroglutamic acid containing the group:

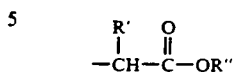

are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above list of specific examples of esters of pyroglutamic acid is not exhaustive, there being many other examples expressed by the generic structure of these esters.

The amount of the esters of pyroglutamic acid or mixtures thereof to be employed in accordance with the invention, will normally be from 0.01 to 99%, preferably from 0.1 to 20% and most preferably from 0.2 to 2% by weight of the composition.

The Non-Aqueous Vehicle

The composition according to the invention also comprises a solid, semi-solid or liquid cosmetically and/or physiologically acceptable non-aqueous vehicle, to enable the ester to be conveyed to the skin or hair at an appropriate dilution. The nature of the vehicle will depend upon the method chosen for topical administration of the composition.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the esters which therefore ensure that they can be applied to and distributed evenly over the skin or hair at an appropriate concentration. The vehicle is preferably one which can aid penetration of the ester into the skin to reach the stratum corneum.

Non-aqueous vehicles that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, sunflower seed oil, evening primrose oil, castor oil, lanolin alcohols, petrolatum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Gelling agents such as soaps and fatty alcohols;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of non-aqueous vehicle in the composition, can comprise the balance of the composition, particularly where little or no other ingredients are present in the composition. Accordingly, the vehicle or vehicles can comprise from 1 to 99.99%, preferably from 50 to 99.5% and ideally from 90 to 99% by weight of the composition.

Perfume

The composition according to the invention can also optionally comprise a perfume in an amount sufficient to make the composition acceptable to the consumer and pleasant to use. Usually, the perfume when present will form from 0.01 to 10% by weight of the composition.

Activity Enhancer

The composition according to the invention can also optionally comprise an activity enhancer, which can be chosen from a wide variety of molecules that can function in different ways to enhance delivery to the stratum corneum, of the ester or to potentiate its activity. Particular classes of activity enhancers include penetration enhancers and cationic polymers.

Penetration Enhancers

As has been stated earlier, the presence of a penetration enhancer can potentiate the benefit of the ester of pyroglutamic acid, by improving its delivery to the stratum corneum.

The penetration enhancer can accordingly function in a variety of ways. It can for example, improve the distribution of the ester on the skin surface or, it can increase its partition into the skin from the composition when applied topically, so aiding its passage to its site of action. Other mechanisms enhancing the benefit of the chemical inhibitor may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
2-hydroxypropanoic acid
2-hyroxyoctanoic acid, Further examples of penetration enhancers include:
Dimethyl sulphoxide N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one Further examples of penetration enhancers include surface active agents, preferred examples of which include:

(i)
Anionic surface active agents, such as metallic or alkanolamine salts of fatty acids for example sodium laurate and triethanolamine oleate;
alkyl benzene sulphonates, for example triethanolamine dodecyl benzene sulphonate;
alkyl sulphates, for example sodium lauryl sulphate;
alkyl ether sulphates, for example sodium lauryl ether sulphate [2 to 8 EO];
sulphosuccinates, for example sodium dioctyl sulphosuccinate;
monoglyceride sulphates, for example sodium glyceryl monostearate monosulphate;
isethionates, for example sodium isethionate;
methyl taurides, for example Igepon T;
acylsarcosinates, for example sodium myristyl sarcosinate;
acyl peptides, for example Maypons and Lamepons;
acyl lactylates,
polyalkoxylated ether glycolates, for example trideceth-7 carboxylic acid;
phosphates, for example sodium dilauryl phosphate.
(ii)
Cationic surface active agents, such as amine salts, for example sapamin hydrochloride;
quartenary ammonium salts, for example Quaternium 5, Quaternium 31 and Quaternium 18;
(iii)
Amphoteric suface active agents, such as imidazol compounds, for example Miranol;
N-alkyl amino acids, such as sodium cocaminopropionate and asparagine derivatives;
betaines, for example cocoamidopropylbetaine
(iv)
Nonionic surface active agents, such as fatty acid alkanolamides, for example oleic ethanolamide;
esters of polyalcohols, for example Span;
polyglycerol esters, for example that esterified with $C_{12-18}$ fatty acids and one or several OH groups;
polyalkoxylated derivatives, for example polyoxy:-polyoxyethylene stearate, and octylphenoxy polyethoxyethanol (TRITON X-100);
ethers, for example polyoxyethylene lauryl ether;
ester ethers, for example Tween;
amine oxides, for example coconut and dodecyl dimethyl amine oxides.

Mixtures of two or more of the above surface active agents can be employed in the composition according to the invention.

(c) cationic polymers chosen from:
Guar Hydroxypropyltrimonium chloride
Quaternium-19
Quaternium-23
Quaternium-40
Quaternium-57
Poly(dipropyldiallylammonium chloride)
Poly(methyl-$\beta$-propaniodiallylammonium chloride;
Poly(diallylpiperidinium chloride)
Poly(vinyl pyridinium chloride)
Quaternised poly (vinyl alcohol)
Quaternised poly (dimethylaminoethylmethacrylate);
and mixtures thereof The amount of activity enhancer, when employed in accordance with the invention, will normally be from 0.1 to 50%, preferably from 0.5 to 25% and most preferably from 0.5 to 10% by weight of the composition.

FURTHER OPTIONAL INGREDIENTS

The composition according to the invention can also optionally contain further ingredients in addition to those which are conventionally used for the provision of the non-aqueous cosmetics acceptable vehicle.

Accordingly, in addition to ingredients conventionally used in preparing a non-aqueous lotion, ointment, gel, powder, solid stick and aerosol concentrate, the composition can optionally comprise further ingredients such as a colourant, preservative, antioxidant, emollient or aerosol propellant, in amounts which are conventional in the cosmetics art.

PREPARATION OF THE COMPOSITION

The composition of the invention can be prepared in the form of a solution, lotion, gel, ointment, solid stick, aerosol or powder, or in any other form suited to administration topically to human skin.

When the composition is a liquid, such as a lotion or aerosol, or a semi-liquid such as a gel or ointment, or a solid stick, then it is usually necessary to dissolve an effective quantity of the ester of pyroglutamic acid, or a mixture thereof, in ethanol or other non-aqueous cosmetically acceptable vehicles, and then to admix this solution, if desired, in a conventional manner with a suitable ointment base containing, for example an oil or silicone oil, or stick base containing a gelling agent such as sodium stearate, or with a normally liquefiable gaseous propellant in order to prepare the composition.

When the composition is a powder, then it is usually necessary to admix the ester of pyroglutamic acid or a mixture thereof, with a powder diluent, such as talc, starch, kaolin, Fuller's earth or other suitable powder base, in order to provide the composition in powder form.

If desired, other cosmetically acceptable carriers, diluents or emollients can be incorporated in the composition according to the invention, in order to facilitate even distribution over the skin or hair at a suitable concentration.

Evidence to support benefit of topical application to skin of the ester of pyroglutamic acid versus the free acid, with particular reference to the preference for employing a non-aqueous vehicle When pyroglutamic acid is applied topically to human skin, only a negligible amount is able to penetrate to the stratum corneum to augment that naturally present in this region of the skin. However, certain esters of pyroglutamic acid are able readily to penetrate the skin to reach the stratum corneum, where naturally occuring esterases cleave the ester to yield the free pyroglutamic acid which can then augment that which is naturally present in the skin, with the consequence that skin benefit is improved.

Delivery of esters of pyroglutamic acid, with subsequent hydrolysis to yield free pyroglutamic acid in the stratum corneum, was confirmed using tritiated esters of pyroglutamic acid and a radio-tracer technique.

Accordingly, [$^3$H] esters of pyroglutamic acid were each dissolved at 1% w/v in anhydrous ethanol or in an oil-in-water emulsion base containing >5% by weight of water. These solutions were then applied to the arms of volunteers, left for 18 hours, washed with soap and water, and the stratum corneum was removed by stripping with Sellotape. The [$^3$H] pyroglutamic acid was separated from unchanged ester by chromotography on AG1X8 resin and the amount delivered to the skin expressed as nmoles per mg of stratum corneum protein.

The result obtained are summarised in Table 1:

TABLE 1

| Ester of Pyroglutamic acid | Pyroglutamic acid delivered (n mol/mg protein) | |
| --- | --- | --- |
| | Ethanol base | Cream base |
| Ethyl | 8 | 5 |
| Butyl | 6 | 2 |
| Hexyl | 5 | 2 |
| Octyl | 4 | 1 |
| Dodecyl | 4 | 1 |

When [$^3$H] pyroglutamic acid instead of a corresponding ester was applied topically in this experiment, a negligible amount of the tritiated free acid was recovered from the stratum corneum.

The above results indicate that pyroglutamic acid is effectively delivered to the stratum corneum following topical application of an ester thereof, while little pyroglutamic acid reached the stratum corneum if applied as the free acid. These results also indicate a preference for a non-aqueous composition, rather than an aqueous cream base. Also, the shorter the alkyl chain of the ester, the more effective is the delivery of the ester to the stratum corneum, as judged by the higher yield of pyroglutamic acid found in that region of the skin.

EXAMPLES

The invention is further illustrated by the following examples.

EXAMPLE 1

Suntan Oil

| Ingredient | % by wt. |
| --- | --- |
| Phase A | |
| propylene glycol myristyl ether | 22.0 |
| cetyl palmitate | 22.0 |
| 2-ethylhexyl methoxycinnamate | 5.0 |
| pyroglutamic acid n-hexyl ester | 5.0 |
| fragrance | 0.1 |
| Phase B | |
| glyceryl sterate | 22.0 |
| mineral oil | 23.9 |

In a vessel, mix in components of Phase A, in order, until all items are dissolved. Upon completion of Phase A, add components in Phase B to those is Phase A and continue mixing until uniform.

EXAMPLE 2

Suntan Oil

| Ingredient | % by wt. |
| --- | --- |
| Phase A | |
| PPG-1 myristyl ether acetate | 22.0 |
| Cetyl palmitate | 22.0 |
| Parsol MCX | 8.0 |
| Benzophenone-3 | 4.0 |
| ethyl-2-[pyroglutamoyloxy]-n-propionate | 1.0 |
| Fragrance | 0.1 |
| Phase B | |
| Glyceryl tiacetyl hydroxysterate | 22.0 |
| PPG-3 hydrogenated castor oil | 20.9 |

In a vessel, mix in components of Phase A, in order, until all items are dissolved. Upon completion of Phase A, add components in Phase B to those in Phase A and continue mixing until uniform.

EXAMPLE 3

Dry Skin Cream

| Ingredient | % by wt |
| --- | --- |
| petrolatum, white USP | 49.9 |
| polyethylene | 3.0 |
| silicone dioxide | 2.0 |
| cyclomethicone | 33.8 |
| dimethicone, 50 cs | 10.0 |
| mineral oil | 1.0 |
| propylparaben | 0.1 |
| sorbic acid | 0.1 |
| fragrance | 0.1 |
| pyroglutamic acid ethyl ester | 1.0 |

Add petrolatum, polyethylene and silicone dioxide to a vessel, heat to 80° C., and homogenize. To this mixture add cyclomethicone, dimethicone, mineral oil, propylparaben and sorbic acid, dissolve and blend, and then cool to 35° C. Dissolve into this mixture PCA ester, and blend until a uniform dry skin composition containing solubilized PCA ester is obtained.

EXAMPLE 4

Dry Skin Lip Balm

| Ingredient | % by wt |
| --- | --- |
| triglycerides | 17.0 |
| trilaurin | 36.7 |
| mineral oil | 9.0 |
| beeswax | 11.0 |
| paraffin | 12.0 |
| petrolatum | 13.0 |
| fragrance/flavour | 0.3 |
| pyroglutamic acid octyl ester | 1.0 |

EXAMPLE 5

Lip Balm

| Ingredient | % by wt |
| --- | --- |
| petrolatum | 51.0 |
| cetyl ester | 9.0 |
| cetyl alcohol | 13.0 |
| oleyl alcohol | 8.0 |
| beeswax | 8.0 |
| mineral oil | 6.0 |

-continued

| Ingredient | % by wt |
|---|---|
| pyroglutamic acid butyl ester | 5.0 |

I claim:

1. In a non-aqueous drug-free composition for topical application to human skin, the improvement which comprises enhanced stability of an ester of pyroglutamic acid and enhanced penetration of said ester to the stratum corneum of the human skin, which composition comprises:

(i) from 0.01 to 99% by weight of an ester of pyroglutamic acid having the structure:

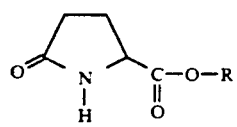 (1)

where R is a linear or branched chain saturated or unsaturated alkyl group having from 1 to 6 carbon atoms; and (ii) from 1 to 99.99% by weight of a cosmetically acceptable non-aqueous vehicle selected from the group consisting of:
petrolatum,
lanolin,
lanolin alcohols,
mineral oil,
sunflower seed oil,
evening primrose oil, and
sesame oil, and mixtures thereof.

2. The non-aqueous composition of claim 1, wherein the amount of the ester of pyroglutamic acid is from 0.01 to 20% by weight of the composition.

3. The non-aqueous composition of claim 1, which additionally comprises from 0.01 to 10% by weight of a perfume.

4. The non-aqueous composition of claim 1, which further comprises 0.1 to 50% by weight of the composition, of an activity enhancer chosen from penetrating enhancers, surface active agents and cationic polymers.

5. The non-aqueous composition of claim 1, wherein the ester of pyroglutamic acid is selected from the group:
pyroglutamic acid methyl ester
pyroglutamic acid ethyl ester
pyroglutamic acid n-propyl ester
pyroglutamic acid n-butyl ester
pyroglutamic acid n-hexyl ester
pyroglutamic acid iso-propyl ester.

* * * * *